United States Patent
Schaffelhofer

(10) Patent No.: US 12,201,378 B2
(45) Date of Patent: Jan. 21, 2025

(54) HYBRID MULTI-CAMERA TRACKING FOR COMPUTER-GUIDED SURGICAL NAVIGATION

(71) Applicant: CORTEXPLORE GMBH, Perg (AT)

(72) Inventor: Stefan Schaffelhofer, Linz (AT)

(73) Assignee: CORTEXPLORE GMBH, Perg (AT)

( * ) Notice: Subject to any disclaimer, the term of this patent is extended or adjusted under 35 U.S.C. 154(b) by 415 days.

(21) Appl. No.: 17/621,331

(22) PCT Filed: Jun. 25, 2020

(86) PCT No.: PCT/AT2020/060253
§ 371 (c)(1),
(2) Date: Dec. 21, 2021

(87) PCT Pub. No.: WO2020/257839
PCT Pub. Date: Dec. 30, 2020

(65) Prior Publication Data
US 2022/0409287 A1    Dec. 29, 2022

(30) Foreign Application Priority Data

Jun. 26, 2019   (AT) ............................. A 50573/2019

(51) Int. Cl.
| | |
|---|---|
| A61B 34/20 | (2016.01) |
| A61B 90/00 | (2016.01) |
| G06T 7/73 | (2017.01) |
| G06T 7/80 | (2017.01) |

(52) U.S. Cl.
CPC ............ *A61B 34/20* (2016.02); *A61B 90/361* (2016.02); *G06T 7/74* (2017.01); *G06T 7/80* (2017.01); *A61B 2034/2057* (2016.02); *A61B 2034/2065* (2016.02); *A61B 2090/367* (2016.02); *A61B 2090/3979* (2016.02); *A61B 2090/3983* (2016.02); *A61B 2560/0223* (2013.01); *G06T 2207/10024* (2013.01); *G06T 2207/10028* (2013.01); *G06T 2207/10048* (2013.01); *G06T 2207/30004* (2013.01); *G06T 2207/30204* (2013.01)

(58) Field of Classification Search
None
See application file for complete search history.

(56) References Cited

U.S. PATENT DOCUMENTS

2018/0153626 A1\*   6/2018   Yang ...................... A61B 5/055
2019/0105514 A1\*   4/2019   Amstutz ................ A61B 34/20

FOREIGN PATENT DOCUMENTS

EP          1933276 A1      6/2008

OTHER PUBLICATIONS

International Search Report and Written Opinion in International Application No. PCT/AT2020/060253, mailed Oct. 22, 2020, 17 pages.

\* cited by examiner

*Primary Examiner* — Dov Popovici
(74) *Attorney, Agent, or Firm* — Liang & Hennessey LLP; Brian Hennessey

(57) ABSTRACT

A camera system for surgical navigation systems including a plurality of cameras mounted in a room. At least three cameras are mounted in the room which are operated in at least two different modes. In the first mode at least a subset of the cameras is operated to determine the position of markers and in a second mode at least a subset of the cameras is operated to determine the position of surfaces of the room.

27 Claims, 4 Drawing Sheets

ХYBRID MULTI-CAMERA TRACKING FOR COMPUTER-GUIDED SURGICAL NAVIGATION

CROSS-REFERENCE TO RELATED APPLICATIONS

The present application is a national phase application of PCT Application No. PCT/AT2020/060253, filed Jun. 25, 2020, entitled "CAMERA SYSTEM", which claims the benefit of Austrian Patent Application No. A 50573/2019, filed Jun. 26, 2019, each of which is incorporated by reference in its entirety.

BACKGROUND OF THE INVENTION

1. Field of the Invention

The invention relates to a hybrid camera system for use in connection with surgical navigation systems.

2. Description of the Related Art

A camera system for use with surgical navigation systems is used to detect the position of objects such as surgical instruments. Due to the application, increased requirements apply to the accuracy as well as fault and failure safety of the system.

In the past, surgical navigation systems have applied a two-camera principle to capture surgical instruments in space. These two cameras are installed in a fixed housing, which is why the relative position and orientation to one another (extrinsic parameters) are known. The position of the instruments/markers "seen" by both cameras in 2D can thus be determined in three dimensions. These systems have several disadvantages. Firstly, the view between one of the two cameras and the instrument to be captured may be obscured, so that no more measurement values are provided. In this case, the 3D detection is completely interrupted. Shocks to the housing, material fatigue or expansion can cause the cameras to move in relation to one another, which has a significant and negative impact on the accuracy of the system and therefore on patient safety. Secondly, these inaccuracies go unnoticed. Thirdly, the measurement volume is reduced to the view of the two cameras and is therefore relatively small.

Known surgical navigation systems work with a camera method that is designed to detect reflective markers on instruments. The reflection occurs in the infrared (IR) region, which is why the cameras can capture the IR light reflected by the markers. The received images are binarized (0=no marker, 1=marker) so that only the markers themselves (position and radius) are determined. Apart from the markers, no image information can be recognized.

However, an additional detection of the environment is of great importance, for example, for the use of robotics and the training of surgeons, as movements of the surgeons can be detected and analysed and/or collisions of a robot with patients or objects can be detected and prevented.

SUMMARY OF THE INVENTION

The object underlying the invention is to create a camera system which is suitable for use with surgical navigation systems, while avoiding the disadvantages mentioned previously.

The method according to the claims is proposed to achieve the object.

In one embodiment, a camera system is proposed comprising at least three cameras, in particular at least four cameras, in which the cameras are operated in at least two different modes, wherein in the first mode (herein referred to as the marker mode) camera settings are used which are optimal or at least more suitable for determining the position of markers from the camera images and in a second mode (herein referred to as the image mode) camera settings are used which are optimal or at least more suitable for determining the position of objects by means of point cloud calculations.

The two modes preferably differ at least in the exposure settings of the cameras. In the marker mode, the contrast between the markers and the background is preferably as strong as possible to enable better or the best possible detection of the markers. The image mode uses settings that allow better or the best possible detection of the background. The two modes also preferably differ in the manner in which the images are processed in the cameras and/or the manner in which the images are transferred from the cameras to a data processing system. Alternatively, or in addition, the manner in which the images taken by the cameras are processed differs.

In one embodiment, at least two cameras are present which are permanently operated in marker mode and at least two further cameras are present which are either permanently operated in image mode or alternatingly operated in marker mode and image mode by time multiplexing.

In one embodiment, a camera system is proposed comprising at least three cameras, in particular at least four cameras, in which the cameras are operated by time multiplexing in at least two different modes, wherein in the first mode camera settings are used which are optimal or at least more suitable for determining the position of the markers from the camera images and in a second mode camera settings are used which are optimal or at least more suitable for determining the position of objects by means of point cloud calculations.

Time multiplexing means that at least one of the cameras, preferably at least a subset of the cameras or all the cameras in an alternating manner, capture images in the first mode for a certain period of time and capture images in at least a second mode for a certain period of time. Preferably, at least one camera alternates between at least two modes over time. Preferably, at least two cameras alternate between at least two modes over time. Preferably, at least three cameras, particularly preferably four cameras, alternate between at least two modes over time. Preferably, at least five cameras, more preferably six cameras, in particular seven cameras, alternate between at least two modes over time.

In particular, the invention may be embodied in the following four variants:

In the first variant, three cameras are mounted in the room, wherein a subset of two cameras is always in marker mode, which subset is composed differently over time. At all times or in time windows with pauses in between one of the cameras is in image mode, wherein which of the cameras is in image mode changes over time. This means that at a first point in time the first and second cameras are in marker mode and the third camera is in image mode and at a second point in time the first camera and the third camera are in marker mode and the second camera is in image mode. Preferably, at a third point in time, the second and third cameras are in marker mode and the first camera is in image mode. Since the images of the image mode of different cameras are acquired with a time delay, the 3D reconstruction in image mode is performed by evaluating time-delayed images, which means that the accuracy of the evaluation can suffer when the object is moving. Preferably, therefore, more than three cameras are present, wherein one of the following variants can be applied.

In the second variant, at least four cameras are mounted in the room, wherein a subset of at least two cameras is always in marker mode, which subset is composed differently over time. At all times or in time windows with pauses in between at least one of the cameras is in image mode, wherein which of the cameras is in image mode changes over time. Preferably, at all times or in time windows with pauses in between at least two of the cameras are in image mode, wherein which of the cameras are in image mode changes over time. This means, for example, that at a first point in time the first and second cameras are in marker mode and the third and fourth cameras are in image mode, and at a second point in time the first and third cameras are in marker mode and the second and fourth cameras are in image mode. Preferably, each of the cameras is switched between marker mode and image mode over time, as this provides the maximum number of viewing angles and therefore the maximum accuracy and size of the measurement volume for each of the two modes.

In the third variant, at least four cameras are mounted in the room, wherein a subset of at least two cameras is always in marker mode, which subset is composed unchanged over time. At least two of the cameras are always in image mode, wherein which of the cameras are in image mode does not change over time.

In the fourth variant, at least four cameras are mounted in the room, wherein a subset of at least two cameras is always in marker mode, which subset is composed unchanged over time. The cameras of the remaining subset, comprising at least two cameras, switch between marker mode and image mode.

Preferably, infrared light sources are installed in the room.

Particularly preferably, the cameras themselves have infrared illuminants. Preferably, the infrared illuminants are arranged in a ring around the lens or objective of the camera in the form of LEDs.

Preferably, the infrared illuminants are operated in the two modes with different exposure parameters, in particular a different luminosity.

Preferably, the marker mode uses an optical filter, in particular a band-pass filter, with transmission in the infrared range.

Preferably, the optical filter can be activated and deactivated.

For this purpose, the camera can have an electrically controlled mechanism to move the filter in front of the lens for activation and to a region next to the lens for deactivation. Alternatively, the filter itself can be activated or deactivated by changing the light transmission of the filter. For example, the light transmission of the filter can be changed by applying a voltage.

In one embodiment, the filter is only in front of the lens in marker mode. Therefore, the optical filter is deactivated when changing from marker mode to image mode and activated when changing from image mode to marker mode. This embodiment has the advantage that the full wavelength spectrum is available in image mode in order to image the surfaces of the 3D space as completely as possible.

In another embodiment, the optical filter can also be located in front of the lens in image mode. This variant has the advantage that switching between the modes can be done independently of the shutter speed of the optical filter and images can be captured in low light conditions or in darkness.

Preferably, the extrinsic parameters and intrinsic parameters of the cameras are known.

Preferably, the extrinsic and preferably also the intrinsic parameters of the cameras are determined in a calibration process in marker mode, so that using these parameters in image mode, surfaces in the operating room can be precisely reconstructed using point cloud computing or measured. The advantage of this is that the extrinsic and intrinsic parameters can be determined more precisely in marker mode than in image mode. This can improve the resolution in the image mode compared to an image mode or point cloud method in which the extrinsic and intrinsic parameters of the cameras are determined in the image mode.

Preferably, the camera calibration determined in marker mode, i.e., the intrinsic and extrinsic parameters, is used to detect the association of individual pixels on images from different cameras in image mode. Preferably, an image mask is created from this, which aligns the image intensity and/or grey values and/or colour values and/or brightness of associated pixels on images from different cameras in order to achieve the highest possible match between the images. The aligned images are fed into the point cloud calculation, wherein this calculation can be performed with less computational effort and/or higher accuracy.

Preferably, the calibration process is automated by a software. Preferably, the calibration process of the cameras is performed continuously in the background, wherein this calibration process can be executed according to known methods.

Preferably, the number of cameras is selected such that both modes can be executed simultaneously by operating a first subset of cameras in the first mode while operating a second subset of cameras in the second mode.

Preferably, the composition of the subsets changes over time. This means that at least one camera belongs to the subset of cameras of the first mode at a first point in time and belongs to the subset of cameras of the second mode at a second point in time, so that the composition of both subsets changes at the time the change is made.

Preferably, for a first period of time, all available cameras are operated in a first mode, whereafter, for a second period of time, a subset of the cameras which is at least two less than the number of all available cameras is operated in a second mode, whereafter, for a third period of time, all available cameras are operated in said first mode, whereafter, for a fourth period of time, a subset of the cameras which is at least two less than the number of all available cameras is operated in said second mode. Preferably, the remaining at least two cameras are operated in the first mode during the third and fourth periods of time. Preferably, the compositions of said subset of cameras in said second period of time and said fourth period of time differ from each other. This means that at least one camera is operated in the first mode during the second period of time, wherein this camera is operated in the second mode during the fourth period of time.

Preferably, at least two of the cameras are always in the first mode, wherein the selection of the at least two cameras from the totality of cameras preferably changes over time.

Preferably, at least two of the cameras are always in the second mode, wherein the selection of the two cameras from the totality of cameras preferably changes over time.

The images from the cameras of the first mode are used to determine high spatial resolution marker positions, wherein images from each camera are preferentially included in the position determination, so that the full number of cameras present contributes to the increase in accuracy. Since each camera is or can be used to determine the marker position, the likelihood increases that at least two cameras will always have a clear view of the markers to be detected, even if there are a large number of people and/or objects in the room, as is common in operating rooms.

The images from the cameras in the second mode are used to determine 3D surfaces in space, wherein images from each camera are preferably included in the position determination, so that the full number of cameras present contributes to the increase in accuracy. Since each camera is or can be used to determine the 3D surfaces in space, the probability increases that at least two cameras will always have a clear view of each surface to be captured. This means that the surfaces of people and objects can be captured from several sides or angles.

Preferably, the exposure setting of the cameras in marker mode and image mode is automated.

For the marker mode, a reference object located in the room with a known geometry and known number of markers allows the exposure parameters of the camera to be set, controlled, or regulated in such a way that the markers stand out optimally from the background and are thus optimally recognisable.

Since the associated pixels in the image mode are known exactly based on the camera parameters (extrinsic, intrinsic parameters) known in the marker mode, this information can be used in the image mode for optimal exposure. The cameras are set in image mode so that associated pixels have the same intensity as far as possible. This increases the quality of the 3D reconstruction using the point cloud method. In addition, point cloud operation is supported by precise calibration in marker mode.

The system according to the invention can preferably be used to detect patient displacements, in particular to detect displacements of markers on the patient.

Previous systems use a reference sensor or marker attached to the patient to detect their position. If there is a displacement of this reference sensor or marker, there will be significant measurement errors that affect patient safety.

The hybrid camera acquisition according to the invention also allows the surface of the patient to be detected and compared with the relative position of the reference sensor or marker. Deviations can thus be detected to trigger error messages and protect the patient.

Preferably, the present system is used as a positioning system of surgical navigation systems, in particular for the planning, simulation and execution of complex procedures performed on the brain.

Preferably, the cameras of the present system are not integrated into a fixed housing, but several individual cameras are used, which are mounted in different locations in the room, in particular in the operating room. The extrinsic parameters of the cameras can be calculated using a rigid body that has at least three reflective markers at a known distance from one another. In this process, the rigid body is moved through the capture area of the cameras. Due to the simultaneous acquisition of the known rigid body by several cameras, their extrinsic parameters (relative position and orientation of the cameras to one another) and also their intrinsic parameters can be determined. Multi-camera methods like this already exist in the virtual reality sector and have probably not yet been used in the operating room for safety reasons. If a single camera is displaced, the calculation of the instrument position in the 3D space is no longer correct.

This problem can be solved in the first camera mode, i.e., the marker mode, if the position of the instruments is calculated using the data from all cameras as well as in parallel or offset in time, using the cross-validation procedure with the data from different camera groups. In one embodiment of the cross-validation procedure, the data of at least one camera, in particular exactly one camera, is excluded from the calculation in order to arrive at the comparison calculation. In another embodiment of the cross-validation method, the data from at least two cameras, in particular exactly two cameras, is used for the comparison calculation. By performing a large number of such comparison calculations, each with different camera groups, displaced or "decalibrated" cameras can be determined by comparing the comparison calculations with each other and/or comparing the comparison calculations with the main calculation. Depending on the computing capacity, the comparison calculations can all be performed in parallel from a data set of all cameras received at one point in time or offset in time, from a historical data set or from a current data set. The cross-validation procedure, in particular the selection of the data of the camera groups for the cross-validation procedure, can thus be performed purely using software. Alternatively, the comparison calculation can be performed in that cameras actually do not provide data, for example in that they do not capture images at comparison times, or in that these images or image data are not being fed into the calculation of the marker positions. In particular, between the time periods of the main calculations in which all cameras provide data for the calculation of the marker positions, there can be comparison times or comparison time periods in which only a subset of the cameras provides data for the calculation of the marker positions. The cameras which do not provide data at the comparison times or comparison time periods can advantageously be operated in another mode, in particular the image mode, wherein the images of these cameras are fed to another calculation, in particular a point cloud calculation. Using the cross-validation procedure, it is systematically possible to detect the displacement of one or more specific cameras. If, for example, there is always a deviation in the instrument position when a specific camera is included in the calculation, it can be concluded that it has displaced in space, i.e., no longer has its original extrinsic parameters.

Alternatively, or in addition, in the first camera mode, the extrinsic parameters and/or intrinsic parameters can be checked via the local marker geometry of objects, in particular instruments: An instrument has several reflective markers attached to the instrument at a fixed distance from one another. This relative position of the markers to each other can in turn be determined in the cross-validation procedure and used for verification purposes. If there are deviations in the marker distances when data from a specific camera is included in the calculations, it can be concluded that the extrinsic parameters of this camera have become displaced. This value also provides evidence of a displacement.

If a displacement is detected according to at least one of the two methods, the displaced camera is excluded (deactivated) from the calculations in order not to falsify the main calculation (calculation based on all cameras).

Preferably, the verifying cross-validations are calculated in the first mode, i.e., in the marker mode, with a lower capture rate (or sampling rate) in the background, compared to the capture rate (or sampling rate) for the position determination of the markers with all available cameras for the first mode.

In a preferred embodiment, the displaced camera is not permanently deactivated, but a calibration process is started. The geometry of any object or instrument visible in the camera area is measured in 3D by means of the functioning cameras, wherein this can be done in the first and/or second mode. For this reason, the geometry of the object or instrument is known, and the displaced camera can be recalibrated (similar to the original calibration procedure), evaluated and reintegrated into the calculation. Preferably, there is at least one object in the room that is provided with at least three markers that are not arranged equidistantly to one another, so that a clear identification of two markers and the determination of the distance of the two markers to one another is possible. As long as two calibrated cameras are available that take 2D images of the markers, the arrangement of the markers in 3D space can be reconstructed and the distance of the two markers to one another can be determined from the images, if this is not known anyway. The camera's view of the markers is known from the 2D image of the displaced camera, so that the current extrinsic parameters of the displaced camera can be calculated from the 2D image of the displaced camera via the determined distance of the two markers and their position in 3D space and/or the position of the two markers in the 2D images of the calibrated cameras.

Preferably, a reference body specially provided for the recalibration of individual cameras is placed in the room, whose three-dimensional dimensions known to the system can be determined via markers in the first mode and/or via its surface detected in the second mode. For example, a known geometry of the reference body is determined in the second mode and used for recalibration. Preferably, however, a known marker arrangement of the reference body is determined in the first mode and used for recalibration, as the accuracy of the calibration in marker mode is usually higher.

Preferably, a displacement of a camera is thus detected in at least one of the two modes and a recalibration routine is then started, which determines the extrinsic parameters in the marker mode again and preferably also the intrinsic parameters and makes these newly determined parameters available to the 3D reconstruction of both modes.

The advantage of these methods is that they not only eliminate the risks of the multi-camera system, but also exceed the standards of the two-camera system, since the parallel operation or time multiplexing of the two modes and the redundant number of cameras allow errors to be detected. Another advantage is that due to the larger number of cameras, the entire room can be imaged by up to 360°, whereas with the two-camera system only one view of the room is acquired.

Preferably, the local marker geometry of objects, instruments or persons can also be checked in the cross-validation procedure. An object, instrument or person has several reflective markers attached to it at a fixed distance from one another. This relative position of the markers to each other can in turn be determined in the cross-validation procedure and used for verification purposes. If there are deviations in the marker distances regardless of which camera subset is used to calculate the position, it can be concluded that at least one marker position on the object has changed and the cause of the displacement does not result from the displacement of a camera.

Preferably, at least 3 high-resolution cameras are positioned in the room. Preferably, a number of 4-12 high-resolution cameras is positioned in the room.

Preferably, the cameras have a total measuring volume of at least 2×2×2 m.

Preferably, the cameras have a frame rate of 180 Hz in marker mode and image mode. Optionally, the refresh rate in image mode can be significantly lower, typically less than 10 Hz.

A position determination software communicates with the cameras to change their exposure and capture settings for both modes and receive their generated images. In two parallel image processing processes, both the 3D positions of markers and the 3D surfaces of the operating room are calculated using the 2D camera images.

Preferably, local positions are determined with accuracies of less than or equal to 250 μm. The local positions are preferably communicated to a neuronavigation software.

In one embodiment, the invention comprises a camera system for surgical navigation systems, comprising a plurality of cameras mounted in a room, wherein at least three cameras are mounted in the room, which are operated in at least two different modes, wherein a determination of the extrinsic and intrinsic parameters of the cameras is performed in the first mode, wherein this is performed on the basis of the position determination of an arrangement known to the system of at least three infrared markers on an object, and wherein in a second mode the surfaces of the room are determined by means of point cloud calculations from the image data of the cameras with inclusion of the extrinsic and intrinsic parameters of the cameras determined in the first mode.

Preferably, a displacement of cameras is detected in the first and/or second mode. Preferably, in the first mode, the extrinsic parameters and preferably also the intrinsic parameters of a displaced camera are determined again and, based on these newly determined parameters, the calculation model of the point cloud calculations is updated.

In one embodiment, the invention comprises a camera system for surgical navigation systems, comprising a plurality of cameras mounted in a room, wherein at least three cameras are mounted in the room, which are operated in at least two different modes, wherein in the first mode the position of infrared markers is determined from the image information of the cameras and in a second mode the position of surfaces of the room is determined from the image information of the cameras, wherein each camera has an optical filter which can be activated and deactivated and which attenuates visible light more strongly than infrared light, wherein the optical filter is active in the first mode and is not active in the second mode.

In one embodiment, the invention comprises a first method for detecting positional displacements of cameras of a camera system for surgical navigation systems, comprising a plurality of cameras mounted in a room, wherein the system is operated in at least a first mode, in which the position of infrared markers is determined from the image information of the cameras, and wherein the system is operated in at least a second mode, in which the surfaces of the room are determined by means of point cloud calculations from the image data of the cameras with inclusion of the extrinsic and intrinsic parameters of the cameras determined in the first mode, wherein at least one object or instrument with at least three infrared markers is present in the room, the spatial arrangement of which relative to one another is stored in the system, wherein at least three cameras are mounted in the room, whose image information of the first mode is used for a main calculation of the object or instrument positions in the room, wherein comparison calculations are performed additionally, for which comparison calculations only the image information of a subset of cameras is used, and wherein in the comparison calculations the spatial arrangement of at least two of said three infrared markers with respect to one another is calculated, wherein the number of cameras of the subset is at least two and at most the total number of cameras minus one, wherein a number of different comparison calculations are performed for subsets with different compositions, which number of different comparison calculations is at least equal to the total number of cameras minus one, and determining which results of the comparison calculations deviate from the stored arrangement of said markers and further determining which of the cameras is involved in all deviating results.

In one embodiment, the invention comprises a second method for detecting positional displacements of cameras of a camera system for surgical navigation systems, comprising a plurality of cameras mounted in a room, wherein the system is operated in at least a first mode, in which the position of infrared markers is determined from the image information of the cameras, and wherein the system is operated in at least a second mode, in which the surfaces of the room are determined by means of point cloud calculations from the image data of the cameras with inclusion of the extrinsic and intrinsic parameters of the cameras determined in the first mode, wherein at least one object or instrument with at least three infrared markers is present in the room, the spatial arrangement of which relative to one another can be calculated by the system, wherein a number of at least four cameras is mounted in the room, the image information of which is used together for a main calculation of an object position of at least a first object in the room, wherein in addition comparison calculations are performed, for which comparison calculations only the image information of a subset of cameras is used and wherein the object position of the first object in the room is also calculated in the comparison calculations, wherein the number of cameras of the subset is at least two and at most the total number of cameras minus one, wherein a number of different comparison calculations are performed for subsets with different compositions, which number of different comparison calculations is at least equal to the total number of cameras, and determining which results of the comparison calculations differ from other comparison calculations and further determining which of the cameras is involved in those comparison calculations whose results differ from all other comparison calculations.

Preferably, in both methods, the displaced camera involved in all deviating results is excluded from the main calculation, wherein the main calculation is further performed with a reduced number of cameras.

Preferably, the main calculation and the comparison calculations are performed according to one of the two methods above as long as at least three cameras are not excluded in the first method and at least four cameras are not excluded in the second method.

Preferably, for the displaced camera involved in all the deviating results, at least the extrinsic parameters are recalculated and stored based on the spatial arrangement of said markers determined by the remaining cameras in the first mode, by or so that the spatial arrangement of said three markers determined using the image information of the displaced camera is brought into agreement with the spatial arrangement of said three markers calculated by the remaining cameras.

Preferably, in the first mode, the main calculation of the remaining cameras uniquely identifies three markers of any object or instrument, calculates the spatial arrangement of at least two of the three markers, and that for the displaced camera, which is involved in all the deviating results, at least the extrinsic parameters are recalculated and stored based on the calculated spatial arrangement of said two markers with respect to one another and the 2D representations of the arrangement of said two markers from at least one of the remaining cameras and the displaced camera, such that the spatial arrangement of said markers determined using the image information of the deviating camera is brought into agreement with the main calculation of the spatial arrangement of said markers.

Preferably, the recalculated and stored extrinsic parameters of the displaced camera are transferred to the calculation model of the main calculation with all cameras and to the models of the comparison calculations with involvement of the displaced camera and the main calculation is subsequently performed again with all cameras.

Preferably, the recalculated and stored extrinsic parameters of the displaced camera are transferred to the calculation model of the second mode.

A preferred application comprises the use of the subject system with holographic glasses (mixed reality glasses) to integrate them into the surgical navigation system. In one embodiment, reflective markers are attached to the holographic glasses, the position of which is determined in marker mode. This allows the viewing direction and thus the perspective of the viewer to be captured with the very precise accuracy and high frame rate of the present camera system in order to display the anatomy of patients from the viewer's perspective with a latency of preferably less than or equal to 5 ms in the mixed reality glasses.

A medical robot can be integrated into the system. The position of the robot's measuring tip is recorded by the present camera system in order to detect and control the robot's joint positions via inverse kinematics. The robot is controlled relative to the anatomy using the good resolution of the camera system, which is preferably less than or equal to 250 μm in 3D space.

BRIEF DESCRIPTION OF THE DRAWINGS

The invention is illustrated with reference to drawings.

DETAILED DESCRIPTION

Figure 1:
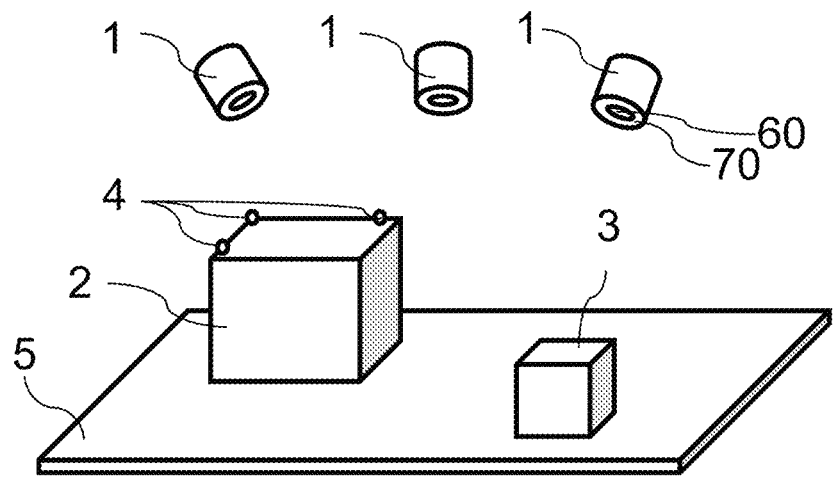
FIG. 1: illustrates an arrangement of cameras in a room to capture objects.

FIG. 1 shows an arrangement of three cameras 1 in a room, which capture images of objects 2, 3 and their surroundings. A first object 2 is provided with markers 4. A second object 3 is present without a marker 4. The objects 2, 3 are arranged on a surface 5 of the room. The cameras 1 capture a series of individual images which are fed into a data processing system. The cameras 1 each have a lens 60, wherein preferably several infrared light sources 70, in particular infrared LEDs, are arranged around the lens 60.

According to the invention, the individual images are captured in at least two different modes, which differ at least in the exposure settings of the cameras 1 or the infrared light sources 70.

Figure 2:
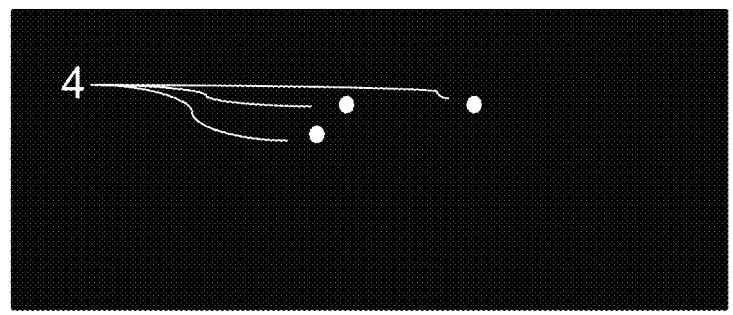
FIG. 2: illustrates the digital reconstruction of 2D marker positions from the cameras' point of view.

FIG. 2 illustrates the reconstructed marker positions based on the images from the cameras in a first mode, herein referred to as marker mode. In marker mode, the infrared light sources 70 are on and illuminate with a first intensity. In marker mode, there is an optical filter in front of the lens, which allows light to pass through comprehensively in the wavelength range of the infrared LEDs. The light from the infrared LEDs is reflected by the small-area markers, wherein the reflected light is detected by the cameras 1. Each camera 1 transmits individual images to a data processing system, wherein the individual images are each as shown in FIG. 2. Therefore, the individual images only contain the information of the marker positions (X,Y coordinates) in the respective individual image. The background is black or so dark that no or no suitable data on the background, i.e., on the surfaces of the room and objects, is available from the individual images. Due to the high contrast between markers and background, marker positions and diameters can be determined in a precise manner.

Alternatively, an initial image analysis can already be performed in the camera 1 or a device located between the camera 1 and the data processing system, so that only the coordinates of the markers 4 in the individual images are sent to the data processing system, which reduces the amount of data to be transmitted. The amount of data transmitted between the cameras 1 and a data processing system is less in the first mode than in the second mode. The computational effort required to determine the marker positions of the first mode is less than the computational effort associated with point cloud computing in the second mode.

In one embodiment, the cameras themselves each have a computing unit that makes camera settings and/or performs the image processing depending on the respective mode. In this case, the camera receives instructions in which mode to capture images at the respective point in time or instructions to change the mode.

The position of the markers 4 in the room can be determined from the coordinates of the markers 4 in the individual images from at least two cameras 1 with known arrangement and orientation in the room. Due to a known arrangement of the markers 4 on the object 2, the position and orientation of the object 2 in the room can be determined from the marker positions.

Figure 3:
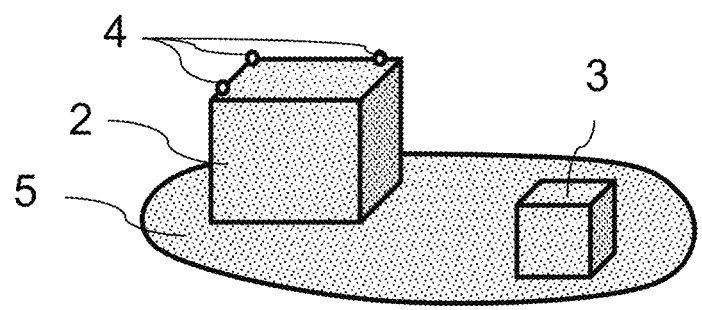
FIG. 3: illustrates the digital reconstruction of objects based on point cloud calculations.

FIG. 3 illustrates a reconstructed 3D image based on the images from the cameras in a second mode, herein referred to as image mode. In this mode, too, the cameras 1 preferably capture individual images, which are transmitted to a data processing system. In the image mode, the infrared light sources 70 preferably illuminate with a second intensity which is different from the first intensity. In image mode, the intensity can be higher to illuminate the room as intensively as possible.

The optical filter is preferably pivoted away from the region in front of the lens 60 so that the entire light spectrum reaches the lens 60 without attenuation by the optical filter.

In the second mode, associated pixels of surfaces are identified by image analysis and their positions are compared in individual images from at least two cameras 1. With the arrangement and orientation of the cameras 1 in the room known, the position and orientation of all surfaces in the room recorded by the cameras can be determined. For example, the object 3 which has no markers 4 becomes visible in the image mode, as does the surface 5, at least as far as it lies within the capture area of at least two cameras 1.

The object 2 with the markers 4 is also visible in image mode, wherein the markers 4 are also visible in image mode. The markers 4 can be 3D objects, preferably in the form of spheres. Two-dimensional markers can also be detected on the object in image mode, provided they are distinguishable in visible light from the surface to which they are attached.

In the second mode, a good contrast between all the different surfaces present in the room is preferred in the images, which is best when the light spectrum is full. The camera images in the second mode are gray scale images and/or preferably color images of the room, which are transmitted in this form to a data processing system.

The transmitted data in both modes contain, in addition to the image data or marker coordinates, information on the time of recording, such as a digital time stamp, so that the images taken at one point in time can be processed together.

Figure 4:
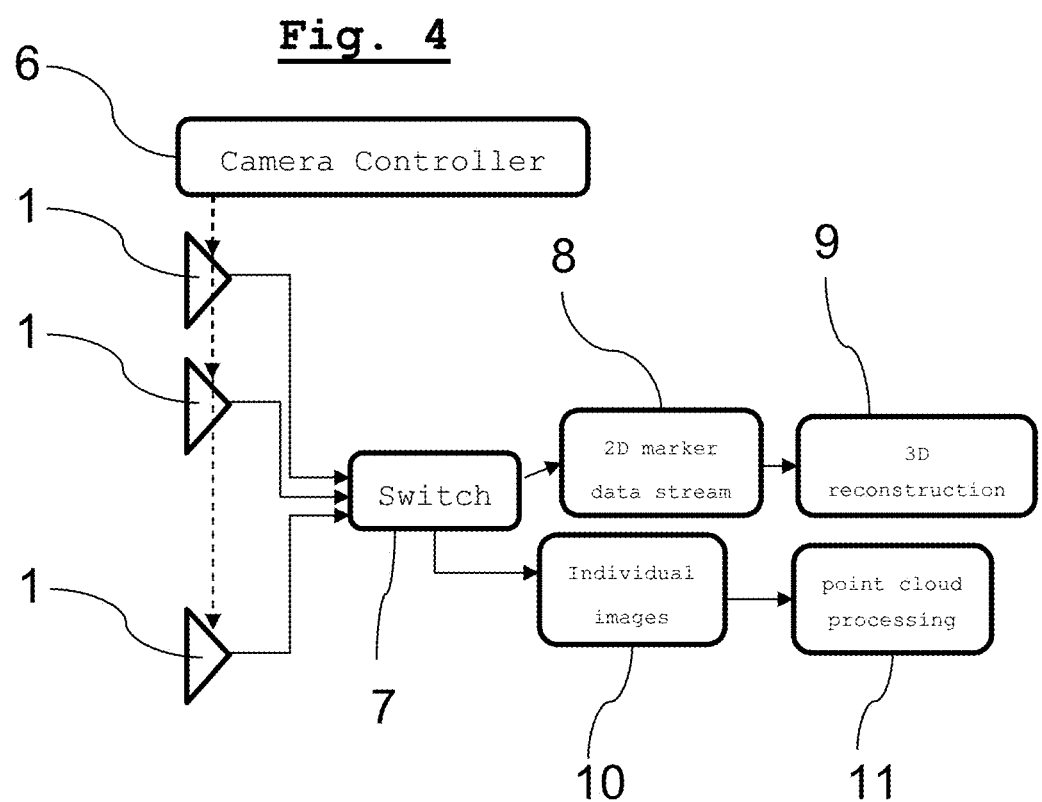
FIG. 4: schematically illustrates a first camera or position detection system according to the invention.

FIG. 4 schematically illustrates a system according to the invention. The cameras 1 and/or the infrared light sources 70 (not shown in FIG. 4) receive settings from a camera controller 6. The settings differ in the two modes. The image information from the cameras 1 reaches a switch 7, which feeds the images or data from the two modes to different processing procedures. The information of the first mode is preferably available as a 2D marker data stream 8, which is fed by the switch 7 to a 3D reconstruction 9 to determine the 3D position of marked objects, in particular instruments, from the marker positions. The 2D marker data stream 8 is understood to mean the continuous transmission of information comprising the marker positions in the images of the cameras 1. The 2D marker data stream 8 can be in the form of frames in which the markers 4 stand out clearly from the background. Preferably, the 2D marker data stream 8 contains the coordinates of all markers in the image area and preferably also the diameter or radius of these markers. Preferably, only this data is included in the 2D marker data stream 8. The coordinates are preferably Cartesian coordinates, in particular x-y coordinates.

Images from the cameras 1 in the second mode, the image mode, are fed by the switch 7 in the form of 2D individual images 10 to a point cloud processing 11, which calculates a 3D point cloud (three-dimensional point cloud) from the individual images 10.

Figure 5:
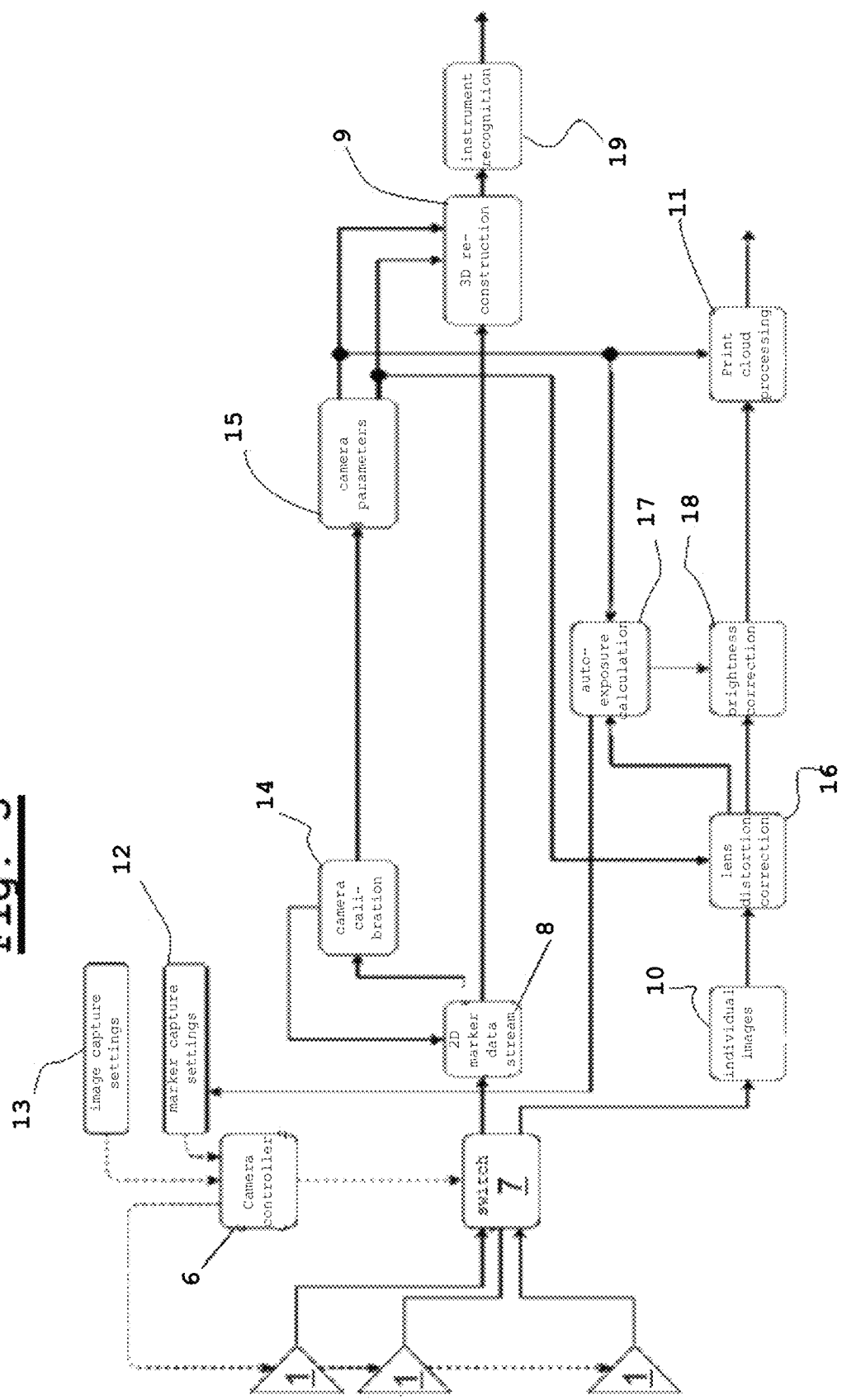
FIG. 5: schematically illustrates a second camera or position detection system according to the invention.

FIG. 5 shows a further embodiment of a system according to the invention. Components 1 and 6 to 11 correspond to those of FIG. 4. The system of FIG. 4 is supplemented by a calibration process in which intrinsic and extrinsic parameters are determined that can be used for camera settings and/or image processing. As illustrated in FIG. 5, the camera controller 6 receives marker capture settings 12 for the first mode and image capture settings 13 for the second mode. The camera controller 6 controls camera parameters selected from the group of camera parameters comprising: exposure time; aperture setting; luminosity of the infrared light sources 70; camera mode; activation/deactivation of the IR filter. Preferably, depending on the camera mode, the images are pre-processed in the cameras 1. Preferably, the cameras 1 have a marker camera mode in which the only information provided to the switch is the marker positions in the image and preferably the respective marker diameter and thus as a 2D marker data stream 8.

FIG. 5 shows the camera calibration 14, which is run at least once when the system is set up or each time it is restarted. A repeated camera calibration 14 while the system is running is also possible. From the camera calibration 14, the camera parameters 15 are obtained, which comprise the intrinsic parameters of the cameras 1, such as lens distortions in particular, and on the other hand comprise the extrinsic parameters of the cameras 1, which extrinsic parameters comprise the position and orientation of the cameras 1 in the room. Camera calibration 14 is performed in marker mode from the data of the 2D marker data stream 8, wherein an object with a known marker arrangement is preferably moved through the room during camera calibration 14.

Once the calibration is complete, the 2D marker data stream 8 is released for processing in the 3D reconstruction 9. Both the extrinsic and intrinsic parameters are used in the 3D reconstruction 9 to determine the 3D marker positions from the 2D marker data stream 8. From the 3D marker positions, the marked objects are recognised by an instrument recognition 19 and markers and/or object positions are determined as a result.

The extrinsic parameters and preferably also the intrinsic parameters are used in point cloud processing 11 to determine the surfaces of objects and of the room. The 3D point cloud resulting from point cloud processing 11 is more accurate than if the extrinsic and intrinsic parameters were determined in image mode, due to the extrinsic and intrinsic parameters that can be determined accurately during calibration in marker mode.

The intrinsic parameters are preferably used to apply a lens distortion correction 16 to the 2D individual images 10, which can already be done prior to the point cloud processing 11.

The extrinsic parameters and/or data from the 2D individual images 10 or the already corrected 2D individual images can be used for the auto-exposure calculation 17. The exposure calculations can be used for marker capture settings 12 and/or image capture settings 13. The exposure calculations can be used for a brightness correction 18 of the 2D individual images 10.

Figure 6:
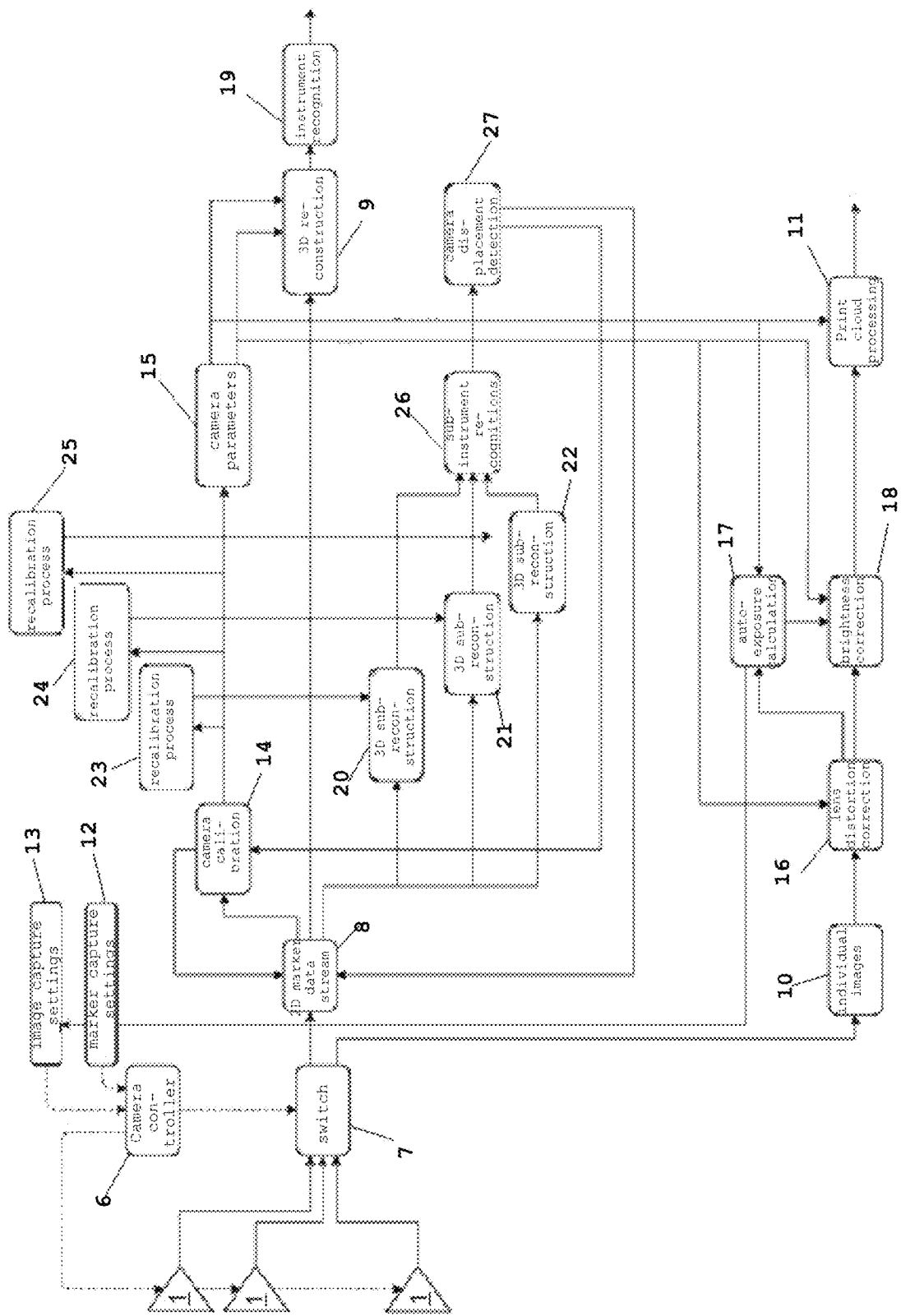
FIG. 6: schematically illustrates a third camera or position detection system according to the invention.

FIG. 6 shows a system based on the system in FIG. 5 wherein a camera displacement detection and a recalibration routine are added. In addition to the main calculation of the 3D reconstruction 9 from the data of all cameras 1, 3D sub-reconstructions 20, 21, 22 are performed, wherein at least two cameras 1 are used for each of these calculations and wherein at least one of the cameras 1 is not included in each of these calculations. For example, in the 3D sub-reconstruction 20, a 3D marker position determination is performed based on the 2D marker data streams 8 from the first and second cameras, while in the second sub-reconstruction 21, a 3D marker position determination is performed based on the 2D marker data streams 8 from the second and third cameras 1. The number of cameras 1 is not limited to three in this regard. The number of 3D sub-reconstructions 20, 21, 22 is at least the number of cameras 1 minus one, wherein each camera is excluded from at least one calculation.

Sub-instrument recognitions 26 are made from the 3D sub-reconstructions 20, 21, 22, wherein a camera displacement detection 27 determines if the sub-instrument recognitions 26 from the sub-reconstructions 20, 21, 22 of different camera pairs or camera subsets differ from one another. In doing so, it is determined under inclusion of the 2D marker data stream 8, which camera 1 exhibits deviations from the other sub-instrument recognitions 26. The camera displacement detection 27 deactivates the displaced camera 1 or interrupts the 2D marker data stream of the displaced camera 1. In the event of deactivation, the 2D individual images 10 of the displaced camera 1 are also no longer fed to the point cloud processing 11. Alternatively, the feeding of the individual images 10 of the displaced camera 1 to the point cloud processing 11 can also be interrupted.

Preferably, the camera displacement detection 27 starts a camera calibration routine which can be executed by the camera calibration 14. In at least one recalibration process 23, 24, 25, the extrinsic and/or intrinsic parameters are recalculated for the displaced camera 1 in marker mode or from the 2D marker data stream 8. The recalculated extrinsic and/or intrinsic parameters are transferred to all affected sub-models of the 3D sub-reconstructions 20, 21, 22 and the main model of the 3D reconstruction 9. Furthermore, the recalculated extrinsic and/or intrinsic parameters are transferred to the model of the point cloud processing 11. The recalibration of cameras 1 of the point cloud processing 11 is thus advantageously performed in marker mode.

Both the 3D sub-reconstructions 20, 21, 22 and, if necessary, the recalibration processes 23, 24, 25 are performed in the first mode with a lower sampling rate than the 3D reconstruction 9 from the data of all or all non-deactivated cameras 1. Preferably, the sampling rate of the 3D reconstruction 9 is greater than or equal to 100 Hz, more preferably greater than or equal to 150 Hz, for example 180 Hz. Preferably, the sampling rate of each of the 3D sub-reconstructions 20, 21, 22 is less than or equal to 10 Hz, more preferably less than or equal to 5 Hz, for example 1 Hz. Preferably, all 3D sub-reconstructions 20, 21, 22 use as a basis for the sub-instrument recognitions 26 and the camera displacement detection 27 the data of the cameras that were captured at the same point in time, wherein the 3D sub-reconstructions 20, 21, 22 can be calculated in parallel to one another. Preferably, the sampling rate of the individual images 10 for the point cloud processing 11 is greater than or equal to 1 Hz, in particular greater than or equal to 10 Hz, in particular greater than 100 Hz, more preferably greater than or equal to 150 Hz, for example 180 Hz.

The invention claimed is:

1. A camera system for surgical navigation systems comprising:
   a plurality of cameras mounted in a room;
   wherein at least three cameras of the plurality of cameras are operated in at least two different modes;
   wherein in a first mode of the at least two different modes, at least a first subset of the at least three cameras is operated to determine a position of markers and in a second mode of the at least two different modes, at least a second subset of the at least three cameras is operated to determine a position of surfaces of the room;
   wherein a composition of the first subset and the second subset changes over time.

2. The camera system as claimed in claim 1, wherein in the first mode at least the first subset is operated with settings which are more suitable with regard to determining the position of the markers and in the second mode at least the second subset is operated with settings which are more suitable with regard to determining the position of the surfaces of the room, in each case with reference to the other of the two modes.

3. The camera system as claimed in claim 1, wherein at least a third subset of of the at least three cameras, comprising at least two cameras, is always operated in the first mode with a different composition of cameras over time.

4. The camera system as claimed in claim 1, wherein at least a third subset of of the at least three cameras, comprising at least two cameras, is always operated in the second mode with a different composition over time.

5. The camera system as claimed in claim 1, wherein a fourth subset of the at least three cameras comprising at least two cameras of the same or different composition over time is operated permanently in one of the two modes, wherein the other mode is operated in time windows with pauses in between.

6. The camera system as claimed in claim 1, wherein all cameras are operated in a single one of the two modes in a time window and in between all cameras are operated in the respective other mode or in between simultaneously a respective subset of the cameras is operated in a respective one of the two modes.

7. The camera system as claimed in claim 1, wherein the camera system is operated according to at least one of the following variants:
in a first variant, three cameras of the plurality of cameras are mounted in the room, wherein a first subset of two cameras of the plurality of cameras is always in marker mode, which first subset is composed differently over time, and wherein always or in time windows with pauses in between the camera not in the first subset is in image mode;
in a second variant, at least four cameras of the plurality of cameras are mounted in the room, wherein a second subset of at least two cameras of the plurality of cameras is always in marker mode, which second subset is composed differently over time, wherein always or in time windows with pauses in between at least one of the cameras not in the second subset is in image mode, wherein which of the cameras not in the second subset is in image mode changes over time, or always or in time windows with pauses in between two of the cameras not in the second subset are in image mode, wherein which of the two cameras is in image mode changes over time;
in a third variant, at least four cameras of the plurality of cameras are mounted in the room, wherein a third subset of at least two cameras of the at least four cameras is always in marker mode, which third subset is composed unchanged over time, and wherein cameras of a remaining subset, comprising at least two cameras, alternate between marker mode and image mode.

8. The camera system as claimed in claim 1, wherein the system comprises infrared light sources, wherein the infrared light sources are operated at different intensities in the at least two different modes.

9. The camera system as claimed in claim 1, wherein:
the plurality of cameras are equipped with an optical filter which allows light in the infrared range to pass and attenuates or eliminates light of other wavelengths; and
the optical filter is active in the first mode and is not active in the second mode.

10. The camera system as claimed in claim 1, wherein:
images from the plurality of cameras of the individual modes are processed differently;
the images made in the first mode are used for 3D reconstruction of positions of the markers; and
the images made in the second mode are used for 3D point cloud calculations.

11. The camera system as claimed in claim 1, wherein in at least one of the two modes a cross-validation of the plurality of cameras is performed in order to detect camera displacements.

12. The camera system as claimed in claim 11, wherein the cross-validation of the plurality of cameras is performed in the first mode.

13. The camera system as claimed in claim 11, wherein in the event of a camera displacement, an affected camera is recalibrated in the first mode.

14. The camera system as claimed in claim 1, wherein:
camera calibration is performed in the first mode; and
intrinsic and extrinsic parameters determined thereby are used to create an image mask for the second mode, said image mask aligning at least one of the image density, grey values, color values and brightness of associated pixels on images of different cameras of the plurality of cameras in order to obtain a highest possible match of the images.

15. The camera system as claimed in claim 1, wherein:
a validation of extrinsic parameters of the plurality of cameras is performed in the first mode;
at one point in time first images of a subset of cameras of the plurality of cameras are used for a first determination of at least one of at least one marker position and an object position, and second images of a second subset of cameras of the plurality of cameras produced at the same point in time are used independently thereof for a second determination of at least one of the at least one marker position and the object position; and
a verification is performed as to whether at least one of the determined marker positions and the object positions of the first and second verifications correspond to one another or to stored values.

16. The camera system as claimed in claim 1, wherein:
at least three cameras are mounted in the room, which are operated in at least two different modes;
a determination of extrinsic and intrinsic parameters of the at least three cameras is performed in the first mode, and on a basis of a position determination of an arrangement known to the system of at least three infrared markers on an object; and
in a second mode surfaces of the room are determined by means of point cloud calculations from image data of the cameras with inclusion of the extrinsic and intrinsic parameters of the at least three cameras determined in the first mode.

17. The camera system as claimed in claim 16, wherein a displacement of cameras is detected in at least one of the first and the second mode and thereupon in the first mode the extrinsic parameters of a displaced camera are determined again and based on these newly determined parameters a calculation model of the point cloud calculations is updated.

18. The camera system as claimed in claim 17, wherein the intrinsic parameters of the displaced camera are determined and based on these newly determined parameters the calculation model of the point cloud calculations is updated.

19. A method for detecting positional displacements of cameras of a camera system for surgical navigation systems, comprising:
mounting a plurality of cameras in a room, wherein the system is operated in at least a first mode, in which positions of infrared markers are determined from image information of the plurality of cameras, and wherein the system is operated in at least a second mode, in which surfaces of the room are determined by means of point cloud calculations from the image information of the plurality of cameras including extrinsic and intrinsic parameters of the plurality of cameras determined in the first mode;

wherein at least one first object or instrument with at least three infrared markers is present in the room, a spatial arrangement of which relative to one another is stored in the system or can be calculated by the system;

wherein the system uses image information from at least three cameras of the plurality of cameras for a first main calculation of a position of the first object or the instrument, or the system uses image information from at least four cameras of the plurality of cameras for a second main calculation of a position of a second object in the room;

wherein further comparison calculations are performed wherein only image information of a subset of cameras of the plurality of cameras is used for the comparison calculations; and wherein in the comparison calculations the position of the first object or the instrument or the second object in the room or the spatial arrangement of at least two of said three infrared markers with respect to one another is calculated; and wherein a number of cameras of the plurality of cameras of the subset is at least two and at most a total number of cameras minus one, wherein a number of different comparison calculations are performed for subsets with different compositions, which number of different comparison calculations is at least equal to the total number of cameras minus one;

determining which results of the comparison calculations deviate from the stored arrangement of said markers or other comparison calculations; and further determining which camera of the subset of cameras is involved in all deviating results or in those comparison calculations whose results deviate from all other comparison calculations.

20. The method as claimed in claim 19, wherein:

at least one object or the instrument with at least three infrared markers is present in the room, the spatial arrangement of which relative to one another is stored in the system, wherein the plurality of cameras is at least three cameras, whose image information of the first mode is used for a main calculation of the object or the instrument positions in the room, wherein comparison calculations are performed additionally, for which comparison calculations only the image information of a subset of cameras is used;

in the comparison calculations the spatial arrangement of at least two of said three infrared markers with respect to one another is calculated;

the number of cameras of the subset is at least two and at most the total number of cameras minus one, wherein a number of different comparison calculations are made for subsets with different compositions, which number of different comparison calculations is at least equal to the total number of cameras minus one, and determining which results of the comparison calculations deviate from the stored arrangement of said markers and further determining which of the cameras is involved in all deviating results.

21. The method as claimed in claim 19, wherein:

at least one object or the instrument with at least three infrared markers is present in the room, the spatial arrangement of which relative to one another can be calculated by the system;

a number of at least four cameras is mounted in the room, the image information of which is used together for a main calculation of an object position of the first or a second object in the room;

in addition comparison calculations are performed, for which comparison calculations only the image information of a subset of cameras is used and wherein the object position of the first or second object in the room is also calculated in the comparison calculations;

the number of cameras of the subset is at least two and at most the total number of cameras minus one; and a number of different comparison calculations are performed for subsets with different compositions, which number of different comparison calculations is at least equal to the total number of cameras, and determining which results of the comparison calculations differ from other comparison calculations and further determining which of the cameras is involved in those comparison calculations whose results differ from all other comparison calculations.

22. The method as claimed in claim 19, wherein:

a displaced camera involved in all deviating results is excluded from the main calculation; and the main calculation is further performed with a reduced number of cameras.

23. The method as claimed in claim 19, wherein for the displaced camera involved in all deviating results, at least the extrinsic parameters are recalculated and stored based on the spatial arrangement of said markers determined by the remaining cameras in the first mode, by or so that the spatial arrangement of said three markers determined using the image information of the displaced camera is brought into agreement with the spatial arrangement of said three markers calculated by the remaining cameras.

24. The method as claimed in claim 23, wherein the recalculated and stored extrinsic parameters of the displaced camera are transferred to the calculation model of the main calculation with all cameras of the plurality of cameras and to the models of the comparison calculations with involvement of the displaced camera, and the main calculation is subsequently performed again with all cameras.

25. The method as claimed in claim 23, wherein the recalculated and stored extrinsic parameters of the displaced camera are transferred to the calculation model of the second mode.

26. The method as claimed in claim 19, wherein in the first mode, the main calculation of the remaining cameras uniquely identifies three markers of any object or the instrument, calculates the spatial arrangement of at least two of the three markers, and that for the displaced camera, which is involved in all the deviating results, at least the extrinsic parameters are recalculated and stored based on the calculated spatial arrangement of said two markers with respect to one another and the 2D representations of the arrangement of said two markers from at least one of the remaining cameras and the displaced camera, such that the spatial arrangement of said markers determined using the image information of the deviating camera is brought into agreement with the main calculation of the spatial arrangement of said markers.

27. A camera system for surgical navigation systems, comprising:

a plurality of cameras mounted in a room;

wherein the plurality of cameras comprises at least four cameras, wherein the at least four cameras are operated in at least in a first mode and in a second mode;

wherein in the first mode at least a first subset of the at least four cameras of the plurality of cameras is operated to determine a position of markers and in a second mode at least a second subset of the at least four cameras is operated to determine a position of surfaces of the room;

wherein the first subset comprises at least two of the at least four cameras, the first subset always operating in the first mode, wherein the first subset is composed unchanged over time;

wherein the second subset comprises at least two of the at least four cameras, the second subset always operating in the second mode;

wherein the second subset is composed unchanged over time;

wherein the at least four cameras, which are not integrated into common fixed housings, are mounted in different locations in the room; and wherein first images from the first subset of the at least four cameras are processed differently to second images from the second subset of the at least four cameras, wherein images of the first subset of the at least four cameras operated in the first mode are used for 3D reconstruction of the position of markers in the room and wherein images from the second subset of the at least four cameras operated in the second mode are used for 3D point cloud calculations.

* * * * *